United States Patent [19]
Frazier

[11] 4,034,763
[45] July 12, 1977

[54] LIGAMENT FORMING SUTURE

[76] Inventor: Calvin H. Frazier, 1808 Verdugo Blvd., Glendale, Calif. 91208

[21] Appl. No.: 694,845

[22] Filed: June 10, 1976

[51] Int. Cl.² ......................................... A61L 17/00
[52] U.S. Cl. ........................................... 128/335.5
[58] Field of Search ..... 128/334 R, 335.5, DIG. 14; 3/1.4

[56] References Cited

U.S. PATENT DOCUMENTS

| | | | |
|---|---|---|---|
| 2,940,247 | 6/1960 | Kirschbaum | 128/335.5 |
| 3,304,557 | 2/1967 | Polansky | 128/334 R X |
| 3,316,557 | 5/1967 | Liebig | 3/1.4 |
| 3,454,011 | 7/1969 | Wagner | 128/335.5 |
| 3,918,455 | 11/1975 | Coplan | 128/335.5 |

FOREIGN PATENT DOCUMENTS 2,508,570  10/1975  Germany .............................. 3/1.4

OTHER PUBLICATIONS

Campbell et al – Trans. A.S.A.I.O. vol. XX-A Apr. 1974, pp. 86–90.

*Primary Examiner*—Dalton L. Truluck
*Attorney, Agent, or Firm*—Robert C. Comstock

[57] ABSTRACT

A suture formed of loosely woven or expanded plastic material, one end of which is swaged to a suturing needle. Upon emplacement in the body, the suture acts initially to hold the tissues in place in a conventional manner. Thereafter it acts to bring about the formation by natural body processes of ligamentous tissue about the suture which supplements and virtually replaces the suture. The suture may be in small diameter tubular form or in small width flat form.

4 Claims, 5 Drawing Figures

LIGAMENT FORMING SUTURE

BACKGROUND OF THE INVENTION

1. Field of the Invention

The invention relates to a suture which when in use in the human body is adapted to form ligamentous tissue.

2. Description of the Prior Art

Sutures formed of various types of plastic material are known in the art. Some of these are designed to remain inert when in use in the body and others are adapted to be absorbed by the body, thereby eliminating the necessity for their physical removal. None of these sutures performs any function or produces any result beyond the physical holding action of a conventional suture. All presently known sutures act merely to hold the tissues together until conventional healing takes place.

Tubes formed of loosely woven or expanded plastic materials such as Dacron and polytetrafluoroethylene have been used as vascular graft loops. It has been noted that the loops, which are substantially porous, have become ingrown with fibrous tissue, some of which is ligamentous in nature. Such vascular prostheses are shown and described in U.S. Pat. Nos. 3,306,557 to Polansky and 3,316,557 to Liebig. These loops also occasionally been used to physically tie down dislocated bones, such as in the shoulder area.

There is presently no suture which has the ability to form ligamentous tissue after its emplacement in the body.

SUMMARY OF THE INVENTION

The present invention contemplates utilizing loosely woven or expanded plastic material as a suture in applications where the formation of ligamentous tissue is desirable. The suture thereby serves a dual purpose, functioning in the first instance as a conventional suture and then serving as a means for bringing about the formation of ligamentous tissue which supplements and eventually replaces the suture and thereafter functions in its place.

In essence, the invention contemplates utilizing plastic material of the type described above which is preferably swaged to a needle and used in the manner of a conventional suture, but in applications where the desirability of forming ligamentous tissue in the suture area is indicated.

It is accordingly the primary object of the present invention to provide a suture which functions initially in the manner of a conventional suture and subsequently in the manner of a ligament.

It is also among the objects of the invention to provide a suture having all of the advantages and benefits of the structure set forth above and described in further detail hereinafter in this specification.

The invention also comprises such other objects, advantages and capabilities as will later more fully appear and which are inherently possessed by the invention.

While there are shown and described herein preferred embodiments of the invention, it should be understood that the same are susceptible of modification and change without departing from the spirit of the invention.

DESCRIPTION OF THE PREFERRED EMBODIMENT

A preferred embodiment which has been selected to illustrate the invention comprises an elongated suture 10, which is swaged at one end thereof to the end of a conventional steel needle 11, being secured to the end thereof which is remote from the point.

Figure 5:
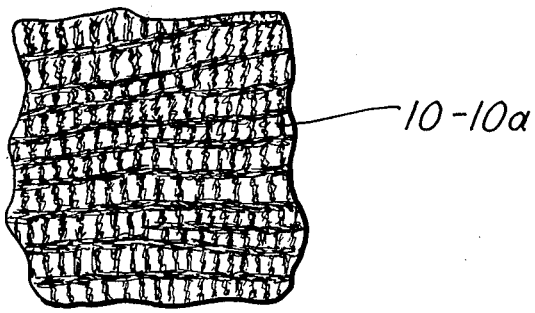
FIG. 5 is a greatly enlarged view of a small piece of expanded porous polytetrafluoroethylene taken from an electron microscopic photograph.

The material from which the suture 10 is formed preferably comprises loosely woven or expanded plastic material such as dacron or polytetrafluoroethylene or other suitable material. The material preferably has sufficient microporosity so that it can and will be penetrated with newly formed tissues after its emplacement in the body. An electron microscopic illustration of expanded porous polytetrafluoroethylene is shown in FIG. 5 of the drawings.

The suture 10 is utilized through conventional suturing techniques in applications where it is desirable that the rupture point or other sutured area become joined with new ligamentous material, which is brought about by the suture itself. Living ligamentous tissue is formed in the sutured area which supplements and eventually replaces the original function of the sutures.

Figure 1:
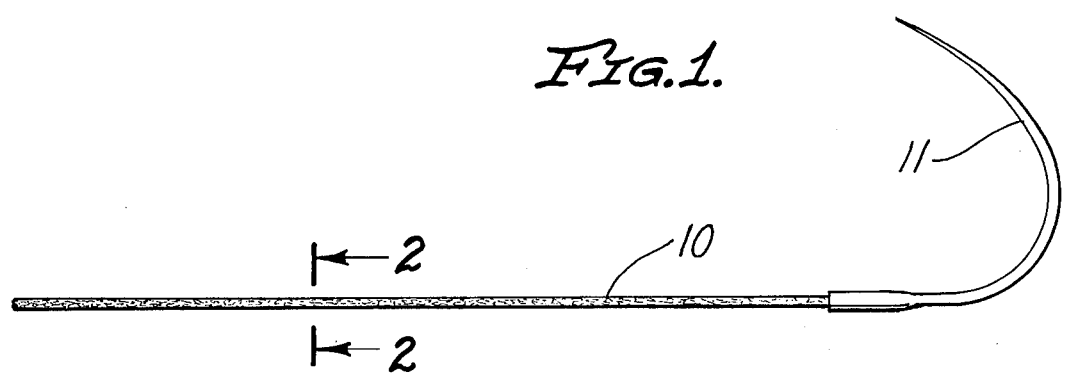
FIG. 1 is an elevational view of a tubular suture swaged to a needle.
Figure 2:
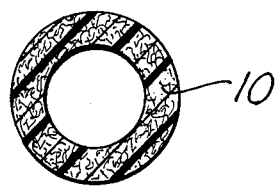
FIG. 2 is a sectional view of the suture, taken on line 2—2 of FIG. 1.
Figure 4:
FIG. 4 is a sectional view of the flat suture, taken on line 4—4 of FIG. 3.
Figure 3:
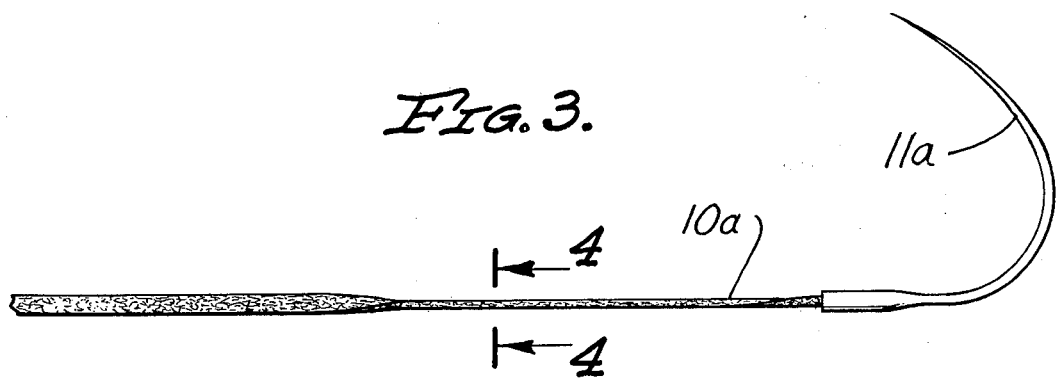
FIG. 3 is an elevational view of an alternative flat suture swaged to a needle.

The suture 10 may be tubular in form, preferably having as small a diameter as is feasible and a wall thickness substantially comparable to that of such materials which are now in use for other purposes, as shown in FIGS. 1-2. An alternative form of suture 10a also comprises a flat piece of the same type of material swaged to a needle 11a, as shown in FIGS. 3-4. The only essential requirements are that the suture be capable of functioning initially in the manner of a conventional suture and thereafter functioning to provide ligamentous tissue in the sutured area.

Since the suture 10 or 10a is swaged to the needle 11 or 11a, there is a smooth transition from the needle to the suture, so that the suture will slide through the tissues easily.

One of the principal advantages and benefits of the present invention is that it brings the suture into the healing process. A conventional suture merely holds the tissues in place and perhaps provokes an inflammatory response or causes the formation of scar tissue. The present suture does far more, by bringing about in the area involved the formation of ligamentous tissue which is "natural" in the sense that it is created by the action of the body itself.

The suture of the present invention may be used to repair torn ligaments at any joint in the body. It may be used to attach an artificial patella to the patellar tendon. It may be used to repair damaged tendons, such as the Achilles tendon. The ligamentous tissue which is formed about the suture is not as good as the structure of the natural tendon. It is, however, better than random scar tissue because the ligamentous tissue tends to line up longitudinally with the suture, which more closely approaches the natural tendon structure.

The suture has an almost unlimited number of applications and may be used wherever the formation of ligamentous tissue about the suture is desirable.

I claim:

1. A suture for attachment to a conventional suture needle for use within a human or animal body, said suture having a minimal outer dimension substantially comparable to that of said needle, said suture having sufficient physical strength to hold together for an extended period of time the members through which it passes, said suture being formed of loosely woven or expanded plastic material having a substantial degree of microporosity sufficient so that upon emplacement within the body said suture becomes penetrated with newly formed ligamentous tissues generated by the body, which ligamentous tissues are adapted to initially act to supplement and reinforce the physical holding action of said suture and which ligamentous tissues over an extended period of time are adapted to replace said suture and thereafter function in place of said suture to physically hold together the members through which said suture initially passed in complete replacement of said suture and its function.

2. The structure described in claim 1, said suture comprising a small diameter tube.

3. The structure described in claim 1, said suture comprising a narrow flat piece of material.

4. The structure described in claim 1, one end of said suture being smoothly swaged to a suture needle.

* * * * *